US006638295B1

(12) United States Patent
Schröer

(10) Patent No.: US 6,638,295 B1
(45) Date of Patent: Oct. 28, 2003

(54) PRESSURE APPLICATION DEVICE AND METHOD FOR AMELIORATING MIGRAINE HEADACHE

(76) Inventor: Frederikus Johannes Schröer, Laurierstraat 89 hs. 1016PJ, Amsterdam, Holland (NL)

( * ) Notice: Subject to any disclaimer, the term of this patent is extended or adjusted under 35 U.S.C. 154(b) by 0 days.

(21) Appl. No.: 09/532,479

(22) Filed: Mar. 22, 2000

Related U.S. Application Data

(63) Continuation-in-part of application No. 09/411,868, filed on Oct. 4, 1999, now abandoned, which is a continuation of application No. PCT/NL98/00449, filed on Aug. 4, 1998.

(51) Int. Cl.[7] .................................................. A61F 5/08

(52) U.S. Cl. .................................... 606/204.15; 602/74

(58) Field of Search ................................ 606/201, 202, 606/203, 204, 204.15, 204.25; 601/132, 134, 135, 120; 128/857; 602/74

(56) References Cited

U.S. PATENT DOCUMENTS 2,482,838 A * 9/1949 Carlson ...................... 601/136
2,567,182 A * 9/1951 Cohen ......................... 606/201
3,884,240 A * 5/1975 Gilman ........................ 128/325
4,571,746 A * 2/1986 Gorike .......................... 2/209
4,597,469 A * 7/1986 Nagashima ................. 181/129
4,920,466 A * 4/1990 Liu ............................ 362/105
5,140,978 A * 8/1992 Sirninger ..................... 128/44
5,405,311 A * 4/1995 Pecora et al. ............... 601/135
5,419,758 A * 5/1995 Vijayan ........................ 602/74
5,700,238 A * 12/1997 Hyson .......................... 602/74
5,792,174 A * 8/1998 Ioan ........................... 606/201
6,034,653 A * 3/2000 Robertson et al. ............. 345/8
6,315,743 B1 * 11/2001 Guest ......................... 601/134

* cited by examiner

*Primary Examiner*—Weilun Lo
*Assistant Examiner*—Linh Truong
(74) *Attorney, Agent, or Firm*—Allen, Dyer, Doppelt, Milbrath & Gilchrist, P.A.

(57) ABSTRACT

Disclosed is an apparatus and method for aiding in compressing an extracranial blood vessel, the apparatus having a biasing member, or spring, for producing a constant force, and two elongated curved arms connected to the biasing member for transmitting the force. The connected arms define a substantially elliptical curve having the biasing member positioned along a major axis of the elliptical curve, and a pressure applicator connected to each arm for applying the force to the skin in the form of pressure, to thereby aid in compressing the underlying blood vessel. Each arm comprises a proximal arm portion connected to the spring, a distal arm portion pivotably connected to the proximal arm portion, and a pressure applicator connected to the distal arm portion. The device is substantially foldable by pivoting each distal arm portion to a position alongside its proximal arm portion, thereby folding the arm. The pressure may be applied with motion to thereby provide a substantially massaging action.

31 Claims, 9 Drawing Sheets

PRESSURE APPLICATION DEVICE AND METHOD FOR AMELIORATING MIGRAINE HEADACHE

This application is a continuation-in-part of U.S application Ser. No. 09/411,868 filed Oct. 4, 1999, now abandoned, which is a continuation of international application PCT/NL98/00449, filed on Aug. 4, 1998, a priority date to which the present application makes claim, and which prior applications are incorporated herein by reference in their entireties.

FIELD OF THE INVENTION

The present invention relates to the field of headaches and, more particularly, to a pressure application device for aiding in compressing an extracranial blood vessel underlying the skin of the head, the device helping to substantially ameliorate a classic migraine headache.

BACKGROUND OF THE INVENTION

Migraine is a periodically recurring headache which generally manifests as a very localized headache. It is estimated that approximately 10% of the population suffers from a more or less serious form of migraine headache.

There are numerous forms of migraine, but generally a classic migraine attack consists of two important, distinct phases. There is a first pre-headache phase, also known by some as the aura stage. The pre-headache stage is often without pain, but with specific pre-headache symptoms. These symptoms may include, for example, visual disturbances including images of colored bubbles, lines and the like, or other disturbances of the various senses, for example in hearing or the senses of taste and smell. Often, a spot of light known as the "aura", is seen by the migraine patient during this pre-headache phase. Numbness or tingling of parts of the body, such as fingers, hands, lips and the like, has also been reported to occur.

In the case of the classical migraine attack, the pre-headache phase is accompanied by vasoconstriction, known to be a constriction of blood vessels in the head, leading to a local increase in blood pressure. In most cases, the pre-headache phase lasts from about 5 to 30 minutes and disappears slowly, together with the other pre-headache symptoms.

While these pre-headache symptoms disappear slowly, they are followed and replaced by the actual headache itself, which is often unbearable for the patient. The migraine headache has a number of frequently occurring side effects, such as nausea, increased sensitivity to light, to noise or to odor, visual disturbances, diarrhea, excessive yawning, sweating and others. Vasodilation is reported to occur during this second phase of the migraine, namely a widening of blood vessels in the head, resulting now in a reduction of local blood pressure.

Because of its frequency and severity, numerous techniques and drugs have been directed in the prior art to counteracting migraine. These, however, typically act during the headache phase. Thus, it is known, for example, to arrange belts providing tension around the head, possibly having discs positioned between the belts, during the headache, as is described in U.S. Pat. Nos. 5,419,758 and 5,897,582, or to administer drugs which counteract the vasodilation.

None of the aforementioned methods or medications actually suppresses pain to a satisfactory extent. Also, it is undesirable to carry out manipulative treatments to the head of a patient during the headache phase, owing to hypersensitivity to external stimuli during the headache.

Surprisingly, it has been found that digital massage applied to the temporal area of the patient during the pre-headache phase may block development of the migraine or substantially ameliorate the symptoms. One possible explanation for this effect may be that if the flow of blood to the head is reduced by vigorous pressure or massage during the phase prior to the actual headache, very little headache occurs during the subsequent headache phase, or the headache is suppressed altogether. Nevertheless, the exact mechanism remains unknown whereby applying pressure and/or massaging the temporal area or other areas of the head is effective in ameliorating or substantially preventing migraine headache in a subpopulation of patients.

SUMMARY OF THE INVENTION

With the foregoing in mind, the present invention therefore provides a pressure application device for use during the phase preceding a headache, and in particular migraine headache, for applying pressure at least locally to one or more extracranial blood vessels adjacently underlying the skin of the head for ameliorating or substantially preventing the occurrence of a migraine headache.

By using the device according to the invention, it is possible to reduce pain during the subsequent headache phase by applying a substantially continuous pressure to certain extracranial blood vessels during the pre-headache phase. An important advantage of the device according to the invention is that headache is substantially prevented or lessened without the use of drugs.

Additionally, the device allows a user to receive constant pressure to the temporal area without requiring use of the hands, and for as long a period of time as necessary, since digital fatigue is avoided. Such prolonged, constant pressure has been found to be important in preventing or lessening the migraine, and has been reported by Lipton in *Annals of Neurology*, Vol. 19, No. 5, May 1986. The present invention, thus, allows the user to discreetly receive preventive treatment while engaged in his or her substantially normal daily activities.

The pressure application device comprises a biasing member, preferably a spring, and specifically a constant force spring for producing a force. An arm is connected to the spring for transmitting the force, and a pressure applicator is connected to the arm for applying the force to the skin in the form of pressure to thereby aid in compressing the blood vessel. A preferred embodiment of the invention has two arms connected to the biasing member for transmitting the force, and a pressure applicator connected to each arm for applying force to the skin in the form of a substantially constant pressure to thereby aid in compressing the blood vessel.

The pressure application device is easily portable by the arms being foldable. The foldable arm comprises a proximal arm portion hingedly connected to the biasing member, a distal arm portion pivotably connected to the proximal arm portion, and a pressure applicator connected to the distal arm portion. The device is thus foldable by pivoting each distal arm portion to a position alongside the proximal arm portion. The folded device may be carried by a user in a pocket sized case, similar in size and appearance to a case for eyeglasses.

The device may additionally be configured to apply pressure with motion to thereby provide a substantially massaging action. In addition, in a preferred embodiment of the device the spring comprises a constant force spring whereby a substantially constant force is produced regardless of displacement. The device is, therefore, able to apply a substantially constant pressure for an indefinite period of time without requiring adjustment or other intervention by the user.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION OF PREFERRED EMBODIMENTS

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Like numbers refer to like elements throughout, and prime notation when used indicates similar elements in alternative embodiments.

Figure 1:
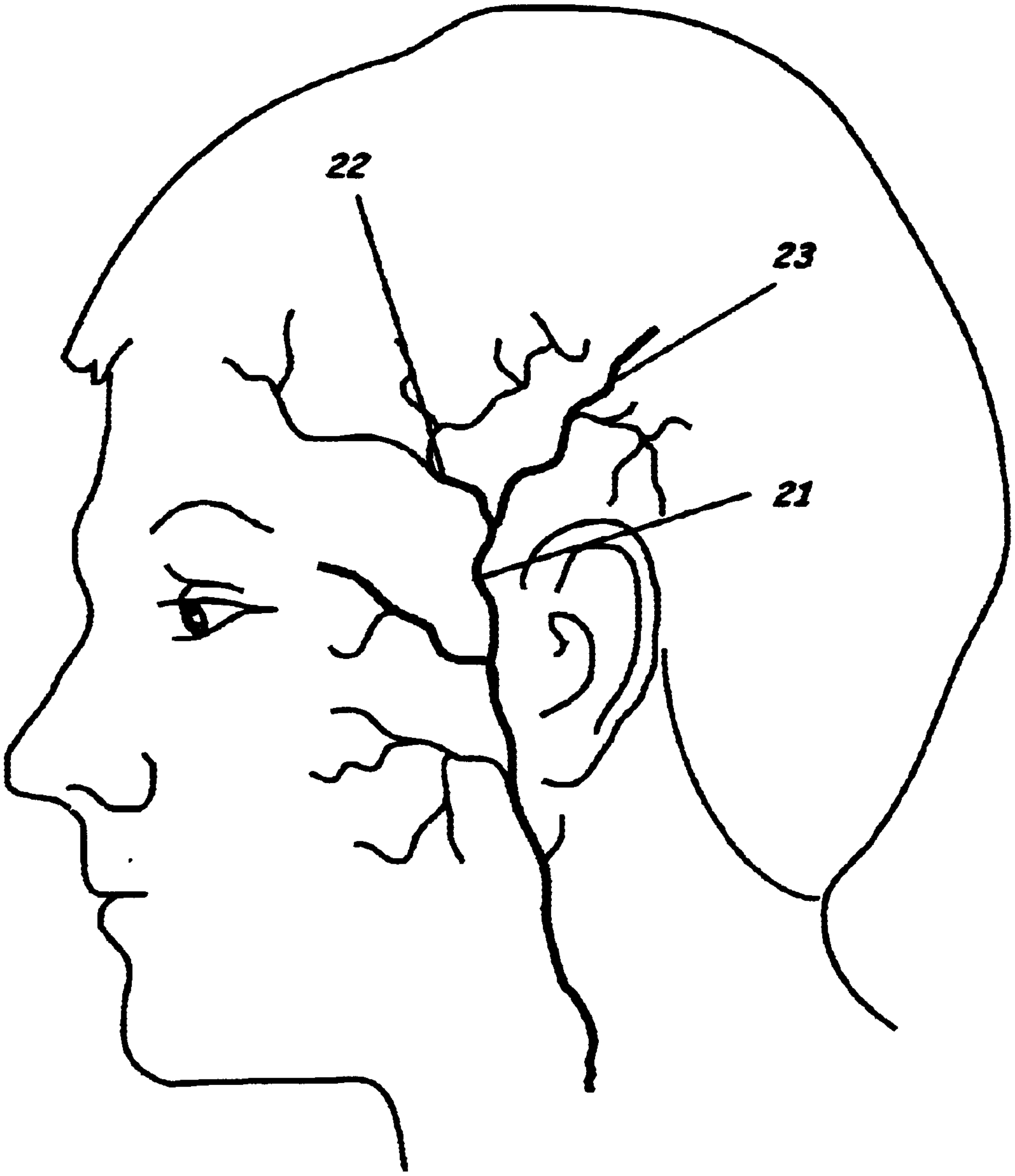
FIG. 1 is a diagrammatic view of a human head, showing the typical relative positions of the temporal blood vessels.

FIG. 1 is a diagrammatic view of a typical human head showing the relative positions of the extracranial blood vessels flowing through the temporal area of the head. The blood vessel 21 typically runs anteriorly to the ear, and diverges into two smaller vessels 22 and 23 above the ear, the smaller vessels respectively running anteriorly and posteriorly on the head, as shown. The skilled artisan will know that this description refers primarily to the use of the invention generally over a temporal blood vessel 21. The invention may, however, be equally applicable to blood vessels positioned adjacently underlying the skin elsewhere in the body. Hence, the term "blood vessel" when used herein may apply to one or to a plurality of blood vessels lying along the temporal area or along other areas of the body.

Figure 2:
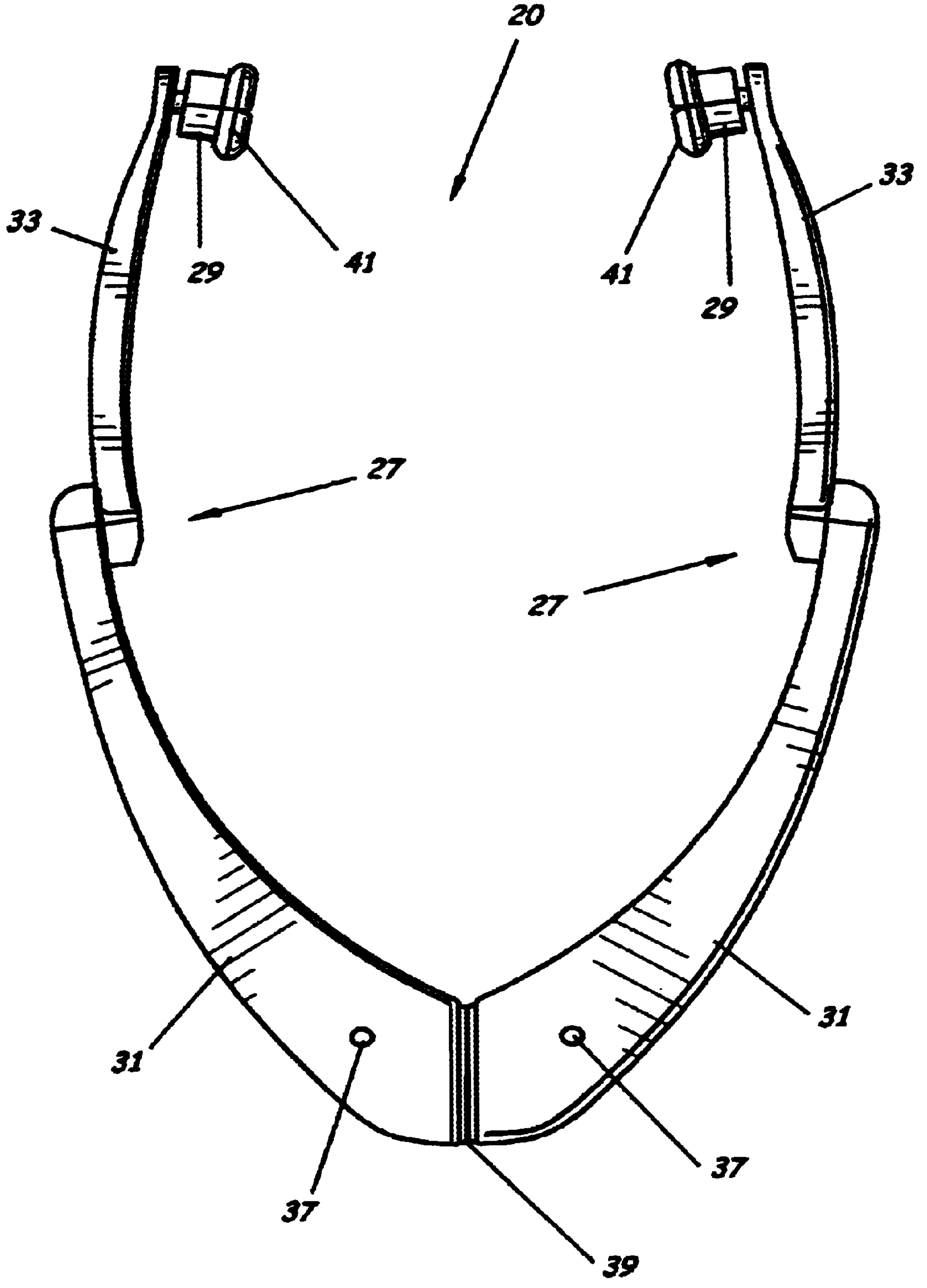
FIG. 2 is a front elevation view of the device according to an embodiment of the present invention.

The invention, shown in FIGS. 2 through 11, comprises a pressure application device 20 for aiding in compressing a blood vessel 21 adjacently underlying the skin. The device comprises a biasing member as known in the art, preferably a spring 25, and more specifically, a helical spring for producing a substantially constant force, an arm 27 connected to the spring 25 for transmitting the force, and a pressure applicator 29 connected to the arm for applying the force to the skin in the form of pressure to thereby aid in compressing the blood vessel 21. The device 20 may further preferably comprise a plurality of arms 27 connected to the spring 25, as shown in FIGS. 2–10, for transmitting the force in more than one direction. In addition, the device 20 may also comprise a plurality of pressure applicators 29 for applying the force as pressure at more than one point on the skin, as seen in FIG. 2.

Advantageously, the pressure may be applied by the device 20 with motion to thereby provide a substantially massaging action. Those skilled in the art will recognize that pressure may be applied with motion in a variety of ways including, for example, in the form of vibrational force, rotational force, alternating pressure and release, or a combination thereof. The skilled worker will also readily understand that known means such as small motors may be included in the device to produce such massaging motion. In addition, in the device 20 the biasing member, or spring 25 preferably produces a substantially constant force and transmits the force to apply a substantially constant pressure for aiding in compressing the blood vessel 21. Those skilled in the art will know that a biasing member which produces a substantially constant force, and particularly a constant force spring, may be produced by known manufacturing methods. A constant force spring, for example, applies a substantially constant force regardless of displacement. Thus, the force applied by the device 20, and consequently the pressure, remains constant regardless of the head size of the user. Moreover, application of a substantially constant force provides the advantage of not requiring manual adjustment by the user, which may result either in insufficient pressure, or in excessive pressure being applied. The pressure applied by the device 20 is preferably in the range of from about 0.01 to about 0.03 newtons per square millimeter. More preferably, the pressure comprises a range from about 0.15 to about 0.025 newtons per square millimeter, and most preferably of about 0.02 newtons per square millimeter. To apply such pressure, the applicator 29 preferably has a surface area of about 200 square millimeters, although the skilled will know that the surface area of the applicator may be of a different dimension.

Figure 8:
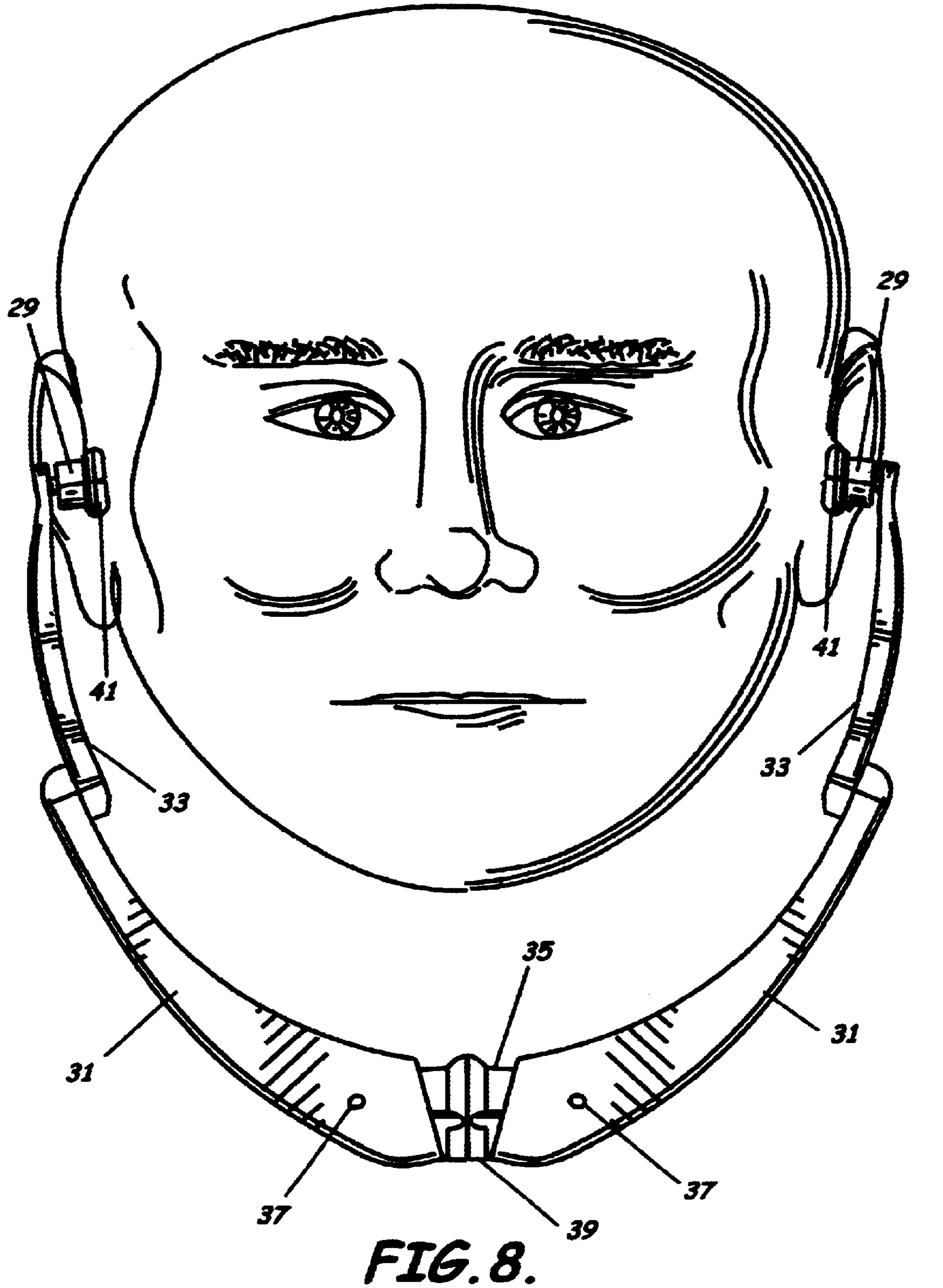
FIG. 8 is a front elevation illustrating one mode in which a user may wear the device of FIG. 2.
Figure 9:
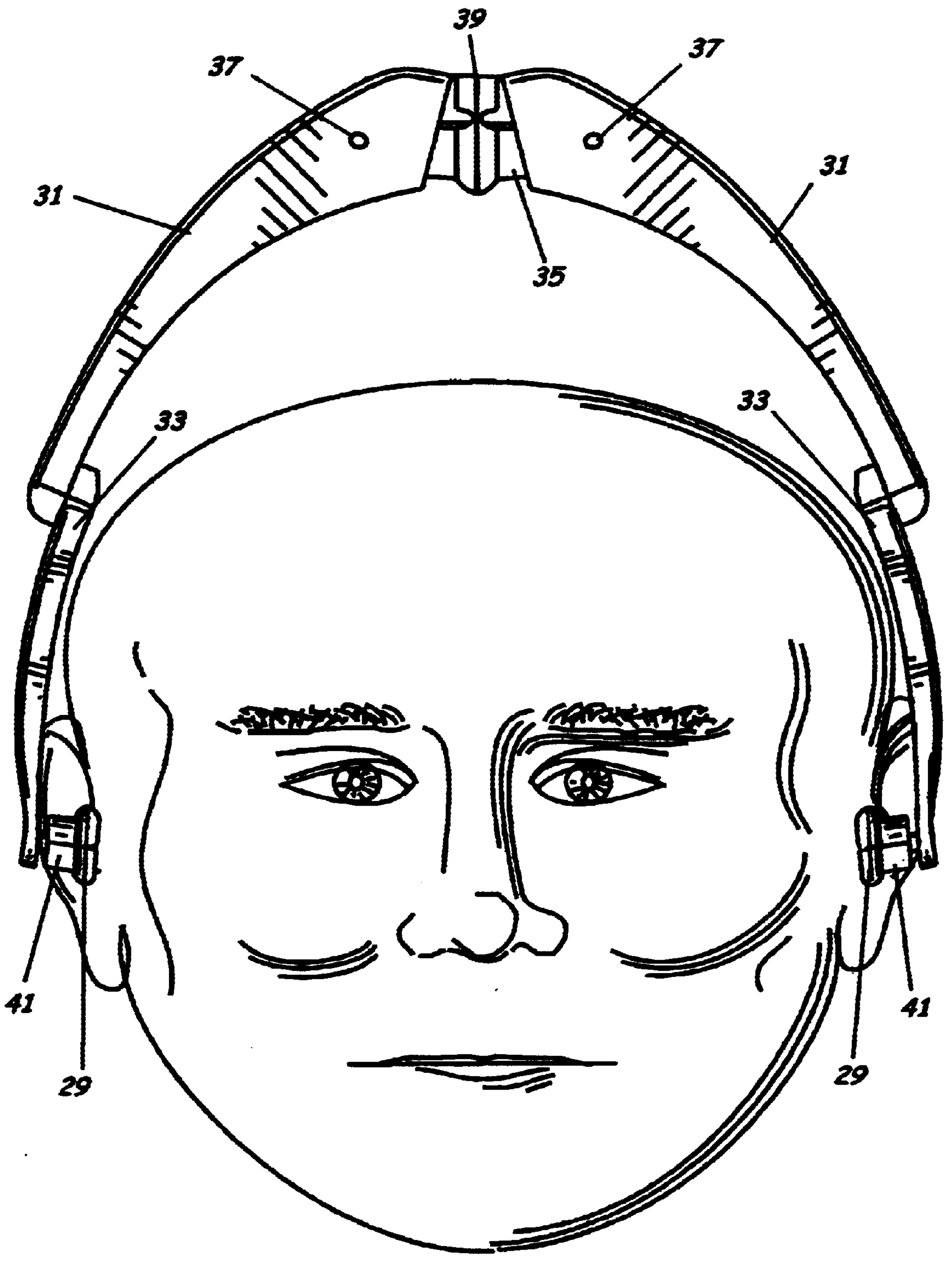
FIG. 9 is a front elevation showing a second mode for wearing the device of FIG. 2.
Figure 10:
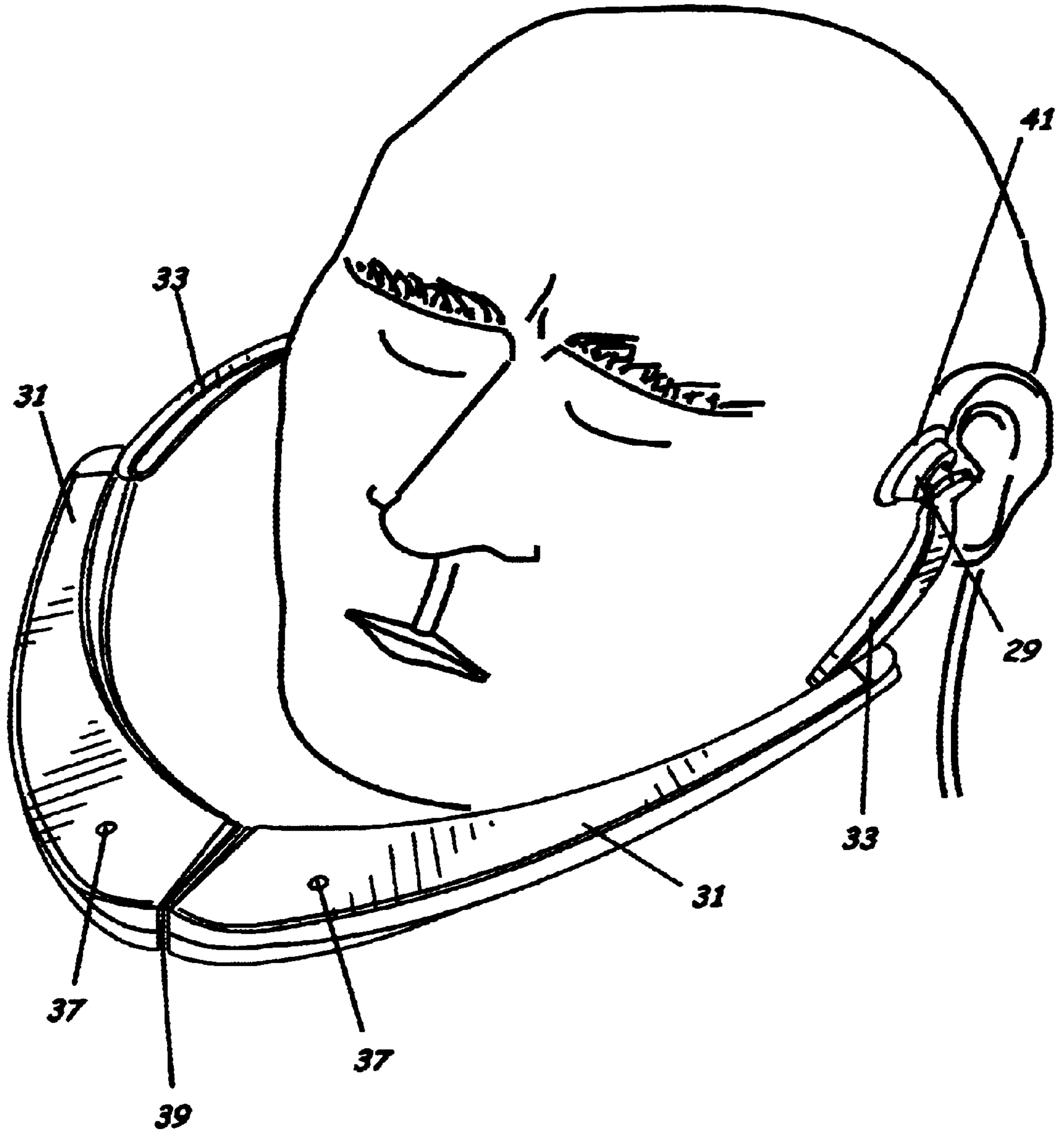
FIG. 10 is a perspective view showing a third mode of wearing the device of FIG. 2.

In another preferred embodiment of the invention, the pressure application device comprises two arms 27 connected to the spring 25 for transmitting the substantially constant force, and a pressure applicator 29 connected to each arm 27 for applying the force to the skin in the form of pressure to thereby aid in compressing the blood vessel 21. The device having two arms 27, each having a pressure applicator 29, advantageously allows the user to position the device 20 so as to apply pressure to both temporal areas simultaneously, as illustrated in FIGS. 8–10.

Figure 5:
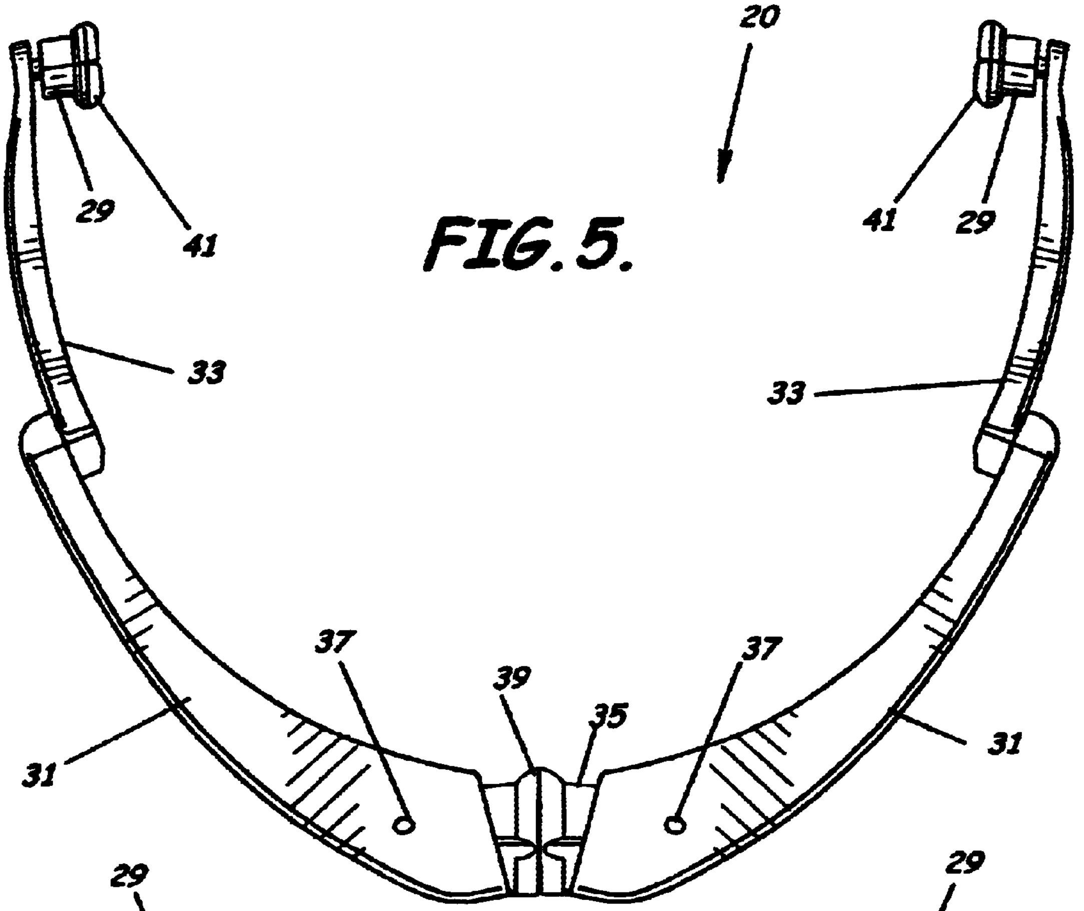
FIG. 5 is the device of FIG. 2 shown with the arms slightly pulled apart, as in preparation for use by a user.
Figure 6:
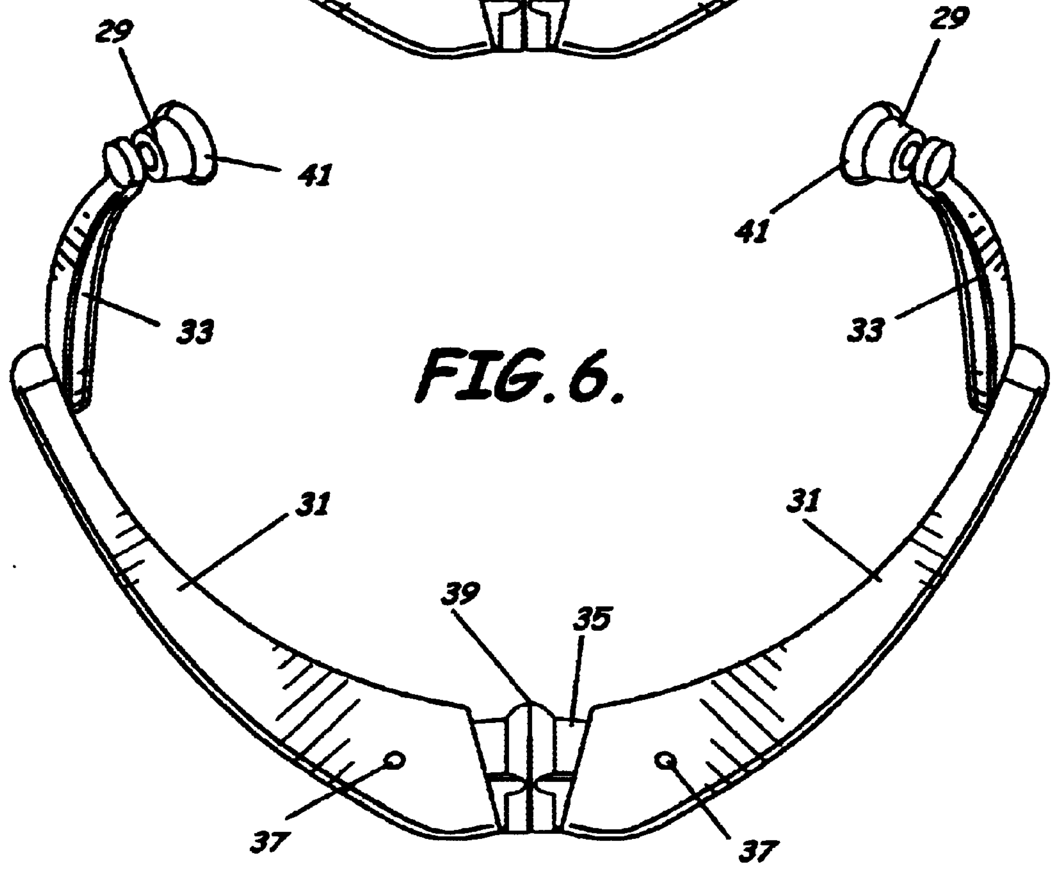
FIG. 6 shows a partially folded configuration of the device, suitable for wear by a user.
Figure 7:
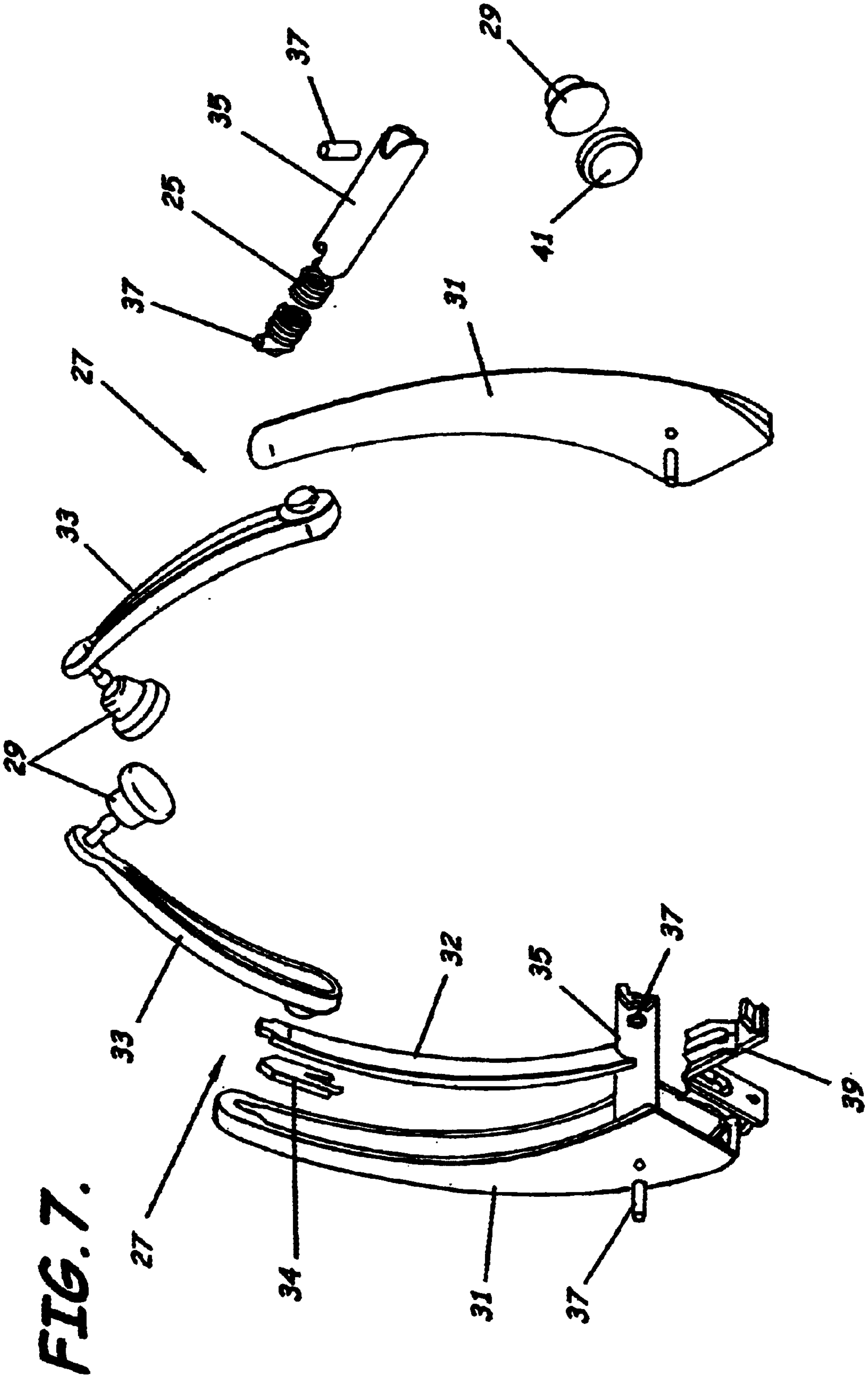
FIG. 7 is an exploded view of the device of FIG. 2.

The pressure application device 20 includes a folding embodiment, as shown in FIGS. 2–10, wherein each arm 27 further comprises a proximal arm portion 31 hingedly connected to the spring 25, a distal arm portion 33 pivotably connected to the proximal arm portion 31, and a pressure applicator 29 connected to the distal arm portion. The pivoting mechanism connecting the proximal and distal arm portions also includes a distal arm pivot click plate 34, shown in FIG. 7, which functions to allow the distal arm portion 33 to pivotably move in defined increments, or clicks. The proximal arm portion 31 also preferably includes a proximal arm cover 32, as shown in FIG. 7. In this embodiment the pressure applicator 29 is preferably connected to the distal arm portion 33 at a point substantially opposite from the point of connection between the distal arm portion and the proximal arm portion 31, as seen in FIG. 7 The arms 27 of the device 20 are preferably also hingedly connected to each other, as shown in FIGS. 4–9. This embodiment of the device also preferably may be disposed to apply pressure with motion to thereby provide a substantially massaging action, and may also comprise a constant force spring 25.

In yet another preferred embodiment, the pressure application device 20 for aiding in compressing an extracranial blood vessel comprises a biasing member, e.g. spring 25, for producing a force, and two elongated curved arms 27 connected to the biasing member for transmitting the force. The connected curved arms define a substantially elliptical curve having the biasing member preferably positioned along a major axis of the elliptical curve, as seen in FIGS. 2 and 5. A pressure applicator 29 is connected to each curved arm for applying the force to the skin in the form of pressure, to thereby aid in compressing the blood vessel. The skilled practitioner will know that an extracranial blood vessel of the head lies outside the skull proper, or cranium, and adjacently underlies the skin so that it is positioned between the skin and the skull.

Figure 3:
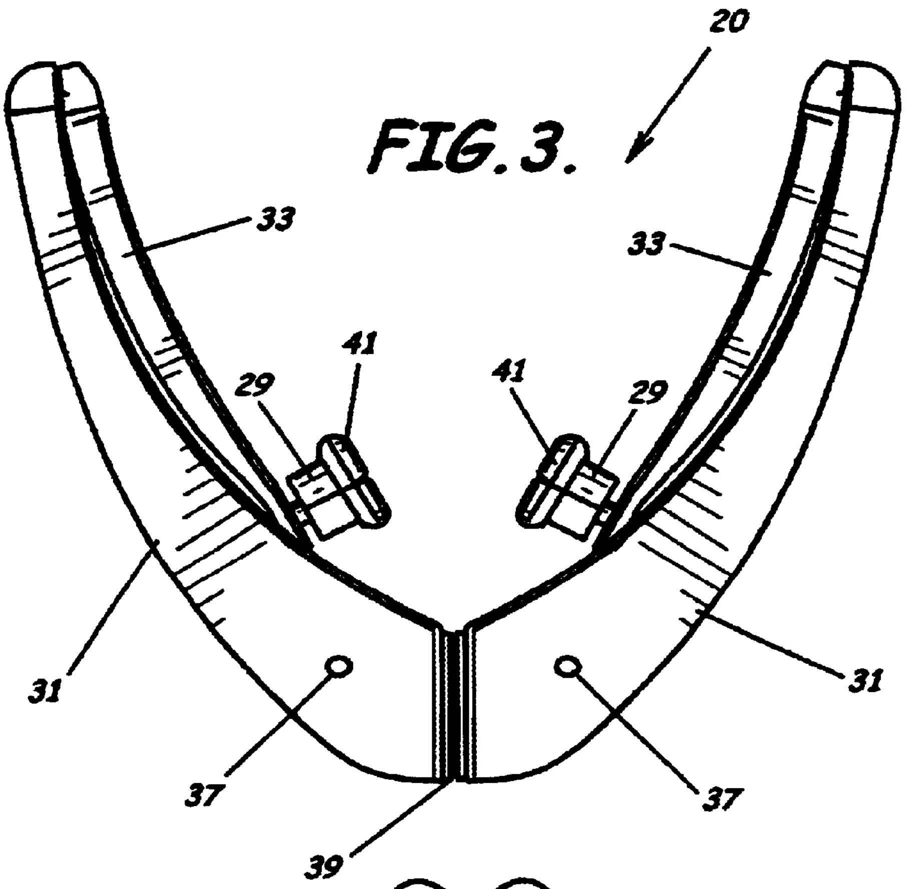
FIG. 3 is the device of FIG. 2 shown in partly folded position.
Figure 4:
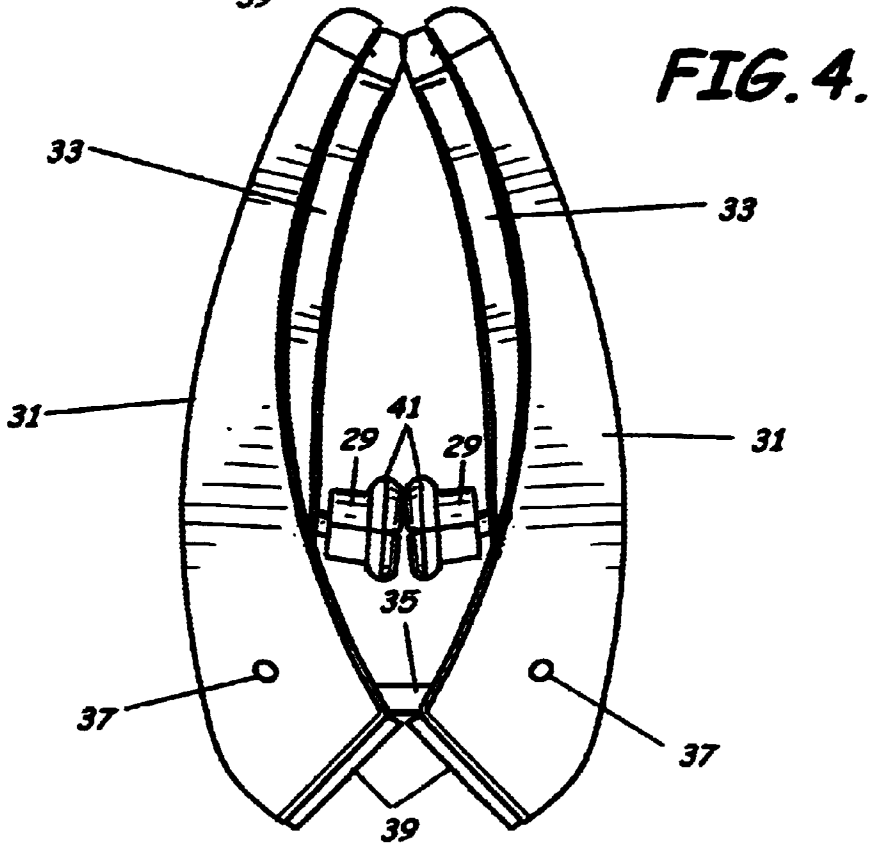
FIG. 4 is the device of FIG. 2 shown in a fully folded position.

This embodiment of the invention also preferably comprises foldable curved arms 27, as shown in FIGS. 3, 4, and 6, wherein each arm further comprises a proximal arm portion 31 hingedly connected to the biasing member, or spring 25, a distal arm portion 33 pivotably connected to the proximal arm portion, and wherein the pressure applicator 29 is connected to the distal arm portion. A preferred hinge connection mechanism is illustrated in FIG. 7, and includes spring 25 positioned within a sleeve 35, and two pins 37 connecting the spring to the arms 27, preferably to the proximal arm portions 31, as shown. The spring 25 produces a force tending to bring the arms 27 together, a force which is applied as pressure when the device is properly worn on the head by a user, as illustrated in FIGS. 8–10. As shown in FIGS. 4–10, the arms 27 are also hingedly connected to each other, preferably by a hinge 39 comprising a resilient plastic material such as polypropylene. The pressure applicator 29, which is preferably connected to the distal arm portion 33 at a point substantially opposite from the point of connection between the distal arm portion and the proximal arm portion 31, as seen in FIG. 2, also preferably includes a cover 41. The cover 41 may be somewhat resilient to provide some distribution of pressure over the temporal area of the user. The cover 41 may also be easily replaceable for sanitary purposes if the device 20 is to be shared among various users. The device is thus foldable by pivoting the distal arm portions 33 to positions alongside the proximal arm portions 31, as shown in FIGS. 3 and 4. This folding action is further aided by the arms 27 being hingedly connected to each other, as seen in FIG. 4, to allow more compact folding. As in other embodiments, the device 20 may preferably apply pressure with motion to thereby provide a massaging action, and may comprise a constant force helical spring 25.

The invention also includes a portable system for compressing an extracranial blood vessel underlying skin on a person's head. The system includes any of the folding embodiments of the pressure application device 20 and a substantially pocket sized carrying case wherein the folded pressure application device may be conveniently carried by the user, the case being somewhat similar to an eyeglass case.

Figure 11:
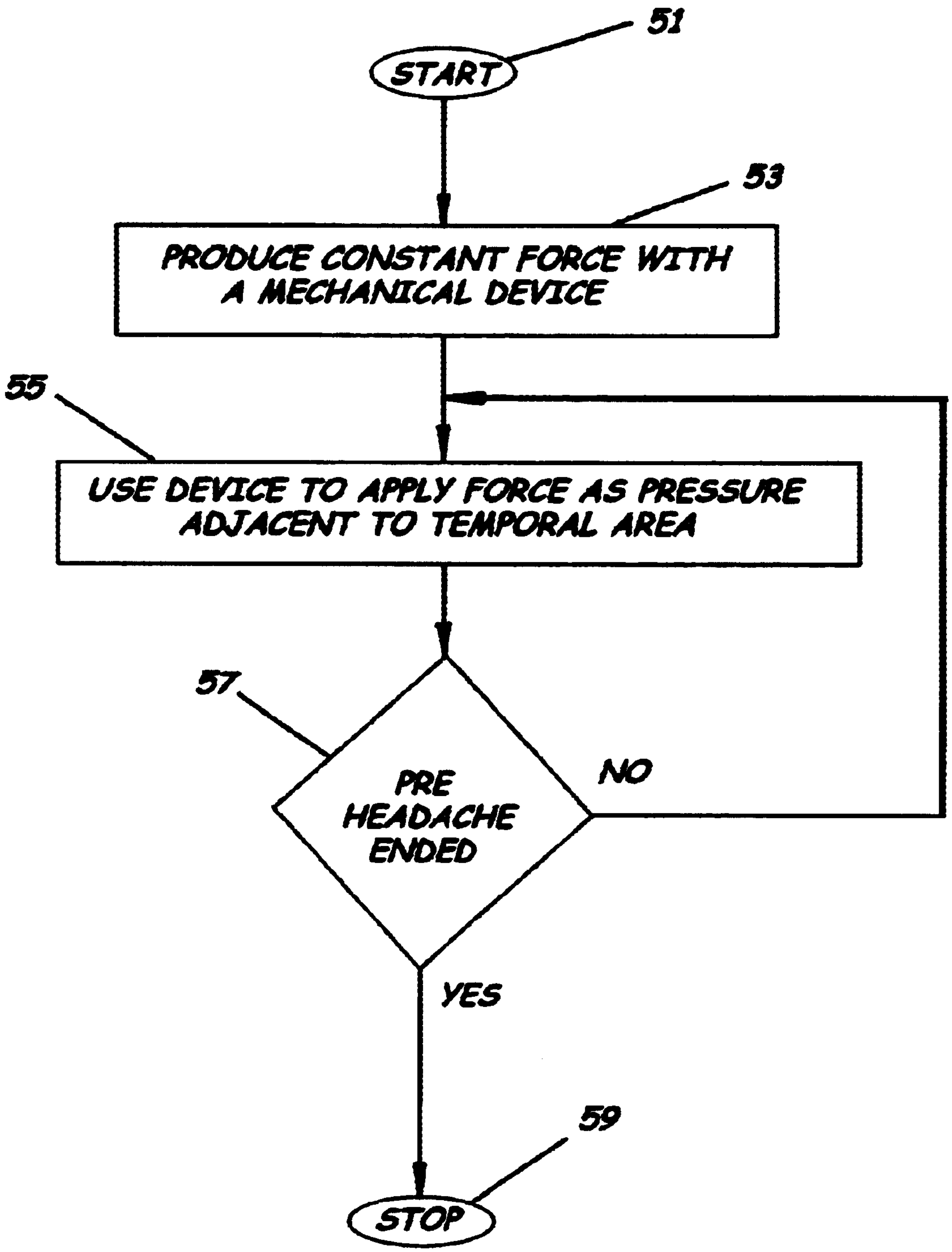
FIG. 11 is a flow diagram illustrating the method of the invention.

The invention also includes method aspects for substantially compressing an extracranial blood vessel as shown in FIG. 11 from the start at Block 51 includes the step of producing a substantially constant force (Block 53) in a mechanical device by a constant force helical spring. The method then follows by applying the constant force (Block 55) on the temporal blood vessel by positioning the mechanical device adjacent thereto so as to apply the force as substantially constant pressure. A preferable force in this method is a substantially constant force of about 5 Newtons.

Additionally included in the invention is a method of treatment for substantially arresting development of a migraine headache, also illustrated in FIG. 11. The method includes from the start (Block 51) using a biasing member in a mechanical device to produce a substantially constant force of about 5 Newtons (Block 53), followed by applying the substantially constant force (Block 55) to a temporal blood vessel during the pre-headache stage of a migraine (Block 57) by positioning the mechanical device adjacent the temporal blood vessel so as to apply the force as substantially constant pressure thereon. The application of pressure is continued until the pre-headache phase ends, the method then stopping at Block 59.

That which is claimed:

1. A pressure application device for substantially compressing an extracranial blood vessel underlying skin on a person's head, said device comprising:

a biasing member generating a constant force;

two elongated arms for transmitting the constant force, each arm having a first end connected to said biasing member by a hinge; and a pressure applicator connected to a second end of each said arm for applying said constant force to skin in the form of constant pressure to thereby aid in compressing the underlying blood vessel.

2. The device of claim 1, wherein said biasing member comprises a helical spring.

3. The device of claim 1, wherein the substantially constant pressure is in a range of from about 0.01 to 0.03 newtons per square millimeter.

4. The device of claim 1, wherein each said arm further comprises a proximal arm portion hingedly connected to said biasing member, a distal arm portion pivotably connected to said proximal arm portion, and wherein said pressure applicator is connected to said distal arm portion.

5. The device of claim 4, wherein said pressure applicator is connected to said distal arm portion at a point substantially opposite from the point of connection between said distal arm portion and said proximal arm portion.

6. The device of claim 4, wherein said device is substantially foldable by pivoting said distal arm portions to positions alongside said proximal arm portions.

7. The device of claim 1, wherein said arms are further hingedly connected to said biasing member.

8. The device of claim 1, wherein said substantially constant pressure is applied with motion so as to thereby provide a massaging action.

9. The device of claim 1, wherein the substantially constant pressure is in a range of from about 0.015 to 0.025 newtons per square millimeter.

10. The device of claim 1, wherein the substantially constant pressure is about 0.02 newtons per square millimeter.

11. A portable system for substantially compressing an extracranial blood vessel on a user's head, said system including:

a foldable pressure application device comprising a constant force biasing member, two foldable elongated arms connected by a hinge to said biasing member for transmitting the constant force as substantially constant pressure, and a pressure applicator connected to each said arm for applying the substantially constant pressure to the head of the user to thereby aid in compressing the blood vessel when said pressure application device is properly positioned on the head; and a substantially pocket sized carrying case for carrying the pressure application device with said two foldable arms in a folded position.

12. A pressure application device for wearing on the head for substantially compressing the temporal areas, said device comprising:

a constant force spring;

two foldable arms connected to said spring for transmitting the constant force as substantially constant pressure;

a hinge connecting said two foldable arms to said spring; and a pressure applicator connected to each said foldable arm for applying the substantially constant pressure to any head size.

13. The device of claim 12, wherein the substantially constant pressure is in a range of from about 0.01 to 0.03 newtons per square millimeter.

14. The device of claim 12, wherein each said foldable arm comprises a proximal arm portion hingedly connected to said spring, and a distal arm portion pivotably connected to said proximal arm portion to thereby fold each said arm substantially in half, and wherein said pressure applicator is connected to said distal arm portion.

15. The device of claim 14, wherein said pressure applicator is connected to said distal arm portion at a point substantially opposite from the point of connection between said distal arm portion and said proximal arm portion.

16. The device of claim 12, wherein said arms are further hingedly connected to each other.

17. The device of claim 12, wherein said substantially constant pressure is applied with motion so as to thereby provide a massaging action.

18. The device of claim 12, wherein the substantially constant pressure is in a range of from about 0.015 to 0.025 newtons per square millimeter.

19. The device of claim 12, wherein the substantially constant pressure is about 0.02 newtons per square millimeter.

20. A pressure application device for substantially compressing a blood vessel adjacently underlying skin, said device comprising:

at least one constant force helical spring;

two arms connected to said at least one helical spring for transmitting the constant force as substantially constant pressure, said two arms connected by a hinge operable along a single imaginary lane coextensive with said two arms; and at least one pressure applicator connected to each said arm for applying the substantially constant pressure on said blood vessel to thereby aid in compressing the blood vessel.

21. The device of claim 20, wherein the substantially constant pressure is in a range of from about 0.01 to 0.03 newtons per square millimeter.

22. The device of claim 20, wherein said substantially constant pressure is applied with motion so as to thereby provide a massaging action.

23. The device of claim 20, wherein the substantially constant pressure is in a range of from about 0.015 to 0.025 newtons per square millimeter.

24. The device of claim 20, wherein the substantially constant pressure is about 0.02 newtons per square millimeter.

25. A method of substantially compressing a temporal blood vessel on a person's head, the method comprising the steps of:

producing a constant force in a biasing member connected to two force transmitting arms by a hinge; and applying the force on the temporal blood vessel as substantially constant pressure by positioning the two force transmitting arms on the person's head so as to apply pressure to the temporal blood vessel.

26. The method of claim 25, wherein the substantially constant pressure is in a range of from about 0.01 to 0.03 newtons per square millimeter.

27. The method of claim 25, wherein the mechanical device for compressing the blood vessel further comprises two elongated curved arms connected to the biasing member for transmitting the force, the arms defining a substantially elliptical curve having the spring positioned along a major axis, and a pressure applicator connected to each arm for applying the force in the form of pressure, to thereby aid in substantially compressing the blood vessel.

28. The device of claim 25, wherein the substantially constant pressure is in a range of from about 0.015 to 0.025 newtons per square millimeter.

29. The device of claim 25, wherein the substantially constant pressure is about 0.02 newtons per square millimeter.

30. A method of treatment during a pre-headache stage of a migraine, the method comprising:

producing a constant force in a biasing member connected to two force transmitting arms by a hinge; and applying the force to a temporal, blood vessel as substantially constant pressure during the pre-headache stage of a migraine by positioning the two force transmitting arms adjacent the temporal blood vessel so as to apply the force as pressure thereon.

31. The method of claim 30, wherein the substantially constant pressure is applied together with motion so as to provide a massaging action to the temporal blood vessel.

* * * * *